(12) United States Patent
Otsuki (10) Patent No.: US 10,520,401 B2
(45) Date of Patent: Dec. 31, 2019

(54) EXHAUST GAS MEASUREMENT SYSTEM AND EXHAUST GAS MEASUREMENT METHOD

(71) Applicant: HORIBA, Ltd., Kyoto (JP)

(72) Inventor: Yoshinori Otsuki, Kyoto (JP)

(73) Assignee: HORIBA, LTD., Kyoto (JP)

( * ) Notice: Subject to any disclaimer, the term of this patent is extended or adjusted under 35 U.S.C. 154(b) by 417 days.

(21) Appl. No.: 15/141,989

(22) Filed: Apr. 29, 2016

(65) Prior Publication Data

US 2016/0319726 A1    Nov. 3, 2016

(30) Foreign Application Priority Data

Apr. 30, 2015    (JP) .................................. 2015-093662

(51) Int. Cl.
  *G01N 1/22*    (2006.01)
  *F01N 11/00*    (2006.01)
  (Continued)

(52) U.S. Cl.
  CPC ........... *G01N 1/2252* (2013.01); *F01N 11/00* (2013.01); *G01N 15/0618* (2013.01); *F01N 3/021* (2013.01); *F01N 2550/04* (2013.01); *G01N 1/2205* (2013.01); *G01N 2001/2264* (2013.01); *G01N 2015/0046* (2013.01)

(58) Field of Classification Search
  CPC ......... G01N 1/2252; G01N 2001/2255; G01N 2001/2264; G01N 15/0618; F01N 11/00
  See application file for complete search history.

(56) References Cited

U.S. PATENT DOCUMENTS

2012/0090377 A1    4/2012   Matsuyama et al.
2012/0225488 A1*   9/2012   Silvis ..................... F01N 3/035
                                                                        436/119
(Continued)

FOREIGN PATENT DOCUMENTS

CN    102918380 A    2/2013
CN    102066900 B    3/2013
(Continued)

OTHER PUBLICATIONS

European Search Report for European Application No. EP 16167449.4, dated Sep. 13, 2016, 7 Pages.
(Continued)

*Primary Examiner* — Nathaniel J Kolb
(74) *Attorney, Agent, or Firm* — Brooks Kushman P.C.

(57) ABSTRACT

In order to secure the dilution ratio accuracy of diluted exhaust gas while making it possible to accurately measure the mass of PM, an exhaust gas measurement system that has a diluted exhaust gas flow path through which the diluted exhaust gas produced by diluting exhaust gas flows and collects particulate matter in the diluted exhaust gas by a filter provided in the diluted exhaust gas flow path for measurement is adapted to include a bypass flow path that branches from the upstream side of the filter in the diluted exhaust gas flow path and merges with the downstream side of the filter; and a separation flow rate control part that while flowing the diluted exhaust gas through the filter, controls the separation flow rate of the diluted exhaust gas flowing through the bypass flow path.

6 Claims, 5 Drawing Sheets

(51) Int. Cl.
*G01N 15/06* (2006.01)
*F01N 3/021* (2006.01)
*G01N 15/00* (2006.01)

(56) References Cited

U.S. PATENT DOCUMENTS

| | | | |
|---|---|---|---|
| 2013/0133440 A1* | 5/2013 | Wei | G01N 1/2252 73/863.03 |
| 2013/0174641 A1 | 7/2013 | Asano et al. | |
| 2015/0153255 A1 | 6/2015 | Asami et al. | |

FOREIGN PATENT DOCUMENTS

| | | |
|---|---|---|
| CN | 103076429 A | 5/2013 |
| CN | 103969088 A | 8/2014 |
| CN | 104075911 A | 10/2014 |
| CN | 104215476 A | 12/2014 |
| CN | 203971918 U | 12/2014 |
| CN | 104364630 A | 2/2015 |
| CN | 102346105 B | 8/2016 |
| EP | 0611962 A1 | 8/1994 |
| EP | 0611962 B1 * | 4/1998 ........... G01N 1/2252 |
| EP | 2418471 A | 2/2012 |
| GB | 2445230 A | 7/2008 |
| JP | 2003-050194 A | 2/2003 |
| JP | 2005-127735 A | 5/2005 |
| JP | 2013-521473 A | 6/2013 |
| JP | 2014-153132 A | 8/2014 |
| WO | 2010-116959 A1 | 10/2010 |
| WO | 2011106850 A | 9/2011 |

OTHER PUBLICATIONS

Office Action dated Aug. 5, 2019 issued for Chinese Patent Application No. 201610247936.3, 9 pgs.
Office Action dated Nov. 12, 2019 issued for Japanese Patent Application No. 2016-038933, 6 pgs.
Ichiro Haga et al., "Analyzing the Emission Gas of An Internal Combustion Car", Railway Research Review, Nov. 2009, pp, 26-29.
Ichiro Haga et al., "Measurement and Evaluation of Exhaust Emissions From Diesel Railcars", Nov. 2009, 5 pgs.

* cited by examiner

EXHAUST GAS MEASUREMENT SYSTEM AND EXHAUST GAS MEASUREMENT METHOD

CROSS-REFERENCE TO RELATED APPLICATION

This application claims priority to JP Application No. 2015-093662, filed Apr. 30, 2015, the disclosure of which is incorporated in its entirety by reference herein.

TECHNICAL FIELD

The present invention relates to an exhaust gas measurement system and exhaust gas measurement method that measure particulate matter contained in the exhaust gas of an internal combustion engine.

BACKGROUND

As this sort of exhaust gas measurement system, as disclosed in JP-A2003-50194, there is one adapted to dilute the exhaust gas of an internal combustion engine at a predetermined dilution ratio to conduct the diluted exhaust gas to a filter, and measure the mass of particulate matter (hereinafter also referred to as PM) in the diluted exhaust gas collected by the filter.

Meanwhile, in a recent PM measuring test, weighting a measurement result depending on a vehicle running mode has been legislated, and for example, the CFR 1066 stipulates that a measurement result in the first running mode (cold start) is given a weight of 0.43, a measurement result in the second running mode (stabilized) is given a weight of 1, and a measurement result in the third running mode (hot start) is given a weight of 0.57.

As such a weighting method, there is a method that measures the mass of PM using one filter for each of the running modes, and multiplies the resulting measurement value by a corresponding one of the above-described weighting values. However, in recent years, PM concentration in exhaust gas has been reduced, and the amount of PM collected by a filter in each running mode is extremely small, making it difficult to accurately measure the mass of the PM.

On the other hand, there is an approved method that weights the flow rate of diluted exhaust gas in each of the running modes, and uses a filter common to the respective running modes to collect PM.

However, if a weighting value is small, this method gives rise to the problem that the diluted exhaust gas flow rate and a diluent gas flow rate fall below the measurement range of a venturi flowmeter suitable to measure each of those flow rates to prevent the respective gas flow rates from being accurately controlled, and therefore the dilution ratio accuracy of the diluted exhaust gas cannot be secured.

SUMMARY OF INVENTION

Technical Problem

Therefore, the present invention is made in order to solve the above-described problems at once, and a main object thereof is to secure the dilution ratio accuracy of diluted exhaust gas while making it possible to accurately measure the mass of PM.

Solution to Problem

That is, an exhaust gas measurement system according to the present invention is one that has a diluted exhaust gas flow path through which diluted exhaust gas produced by diluting exhaust gas flows and collects particulate matter in the diluted exhaust gas by a filter provided in the diluted exhaust gas flow path for measurement, and includes: a bypass flow path that branches from the upstream side of the filter in the diluted exhaust gas flow path and merges with the downstream side of the filter; and a separation flow rate control part that while flowing the diluted exhaust gas through the filter, controls the separation flow rate of the diluted exhaust gas flowing through the bypass flow path.

Such an exhaust gas measurement system can weight the flow rate of the diluted exhaust gas flowing through the filter by controlling the separation flow rate, and can therefore collect the PM using the filter common to respective running modes and accurately measure the mass of the PM.

In addition, since the bypass flow path branches from the upstream side of the filter in the diluted exhaust gas flow path and merges with the downstream side of the filter, only the flow rate of the diluted exhaust gas flowing through the filter can be weighted without changing the total flow rate of the diluted exhaust gas, and even when using venturi flowmeters to measure the diluted exhaust flow rate and a diluent gas flow rate, the dilution ratio accuracy of the diluted exhaust gas can be secured.

In order to control the flow rate of the diluted exhaust gas flowing through the filter in accordance of a test condition stipulated in regulations, emissions measurement regulations, or the like, preferably, a flow rate condition on the flow rate of the diluted exhaust gas to be flowed through the filter is determined in accordance with a preset test condition, and the separation flow rate control part obtains test condition data indicating the test condition, and on the basis of the flow rate condition, controls the separation flow rate.

Specific embodiments includes one in which the test condition data is data including multiple running modes each indicating a vehicle running state and weighting values predetermined for the respective running modes; and the flow rate condition is determined on the basis of the weighting values.

In order to accurately measure the mass of the PM, it is preferable that in all the running modes, the diluted exhaust gas flows through a common filter.

Also, an exhaust gas measurement method according to the present invention is one that uses an exhaust gas measurement system that has a diluted exhaust gas flow path through which diluted exhaust gas produced by diluting exhaust gas flows and collects particulate matter in the diluted exhaust gas by a filter provided in the diluted exhaust gas flow path for measurement. In addition, the exhaust gas measurement system includes a bypass flow path that branches from the upstream side of the filter in the diluted exhaust gas flow path and merges with the downstream side of the filter. Further, the exhaust gas measurement method includes: a first running step of flowing the diluted exhaust gas through the filter at a first flow rate; a second running step of controlling the separation flow rate of the diluted exhaust gas flowing through the bypass flow path and flowing the diluted exhaust gas through the filter at a second flow rate; and a measurement step of measuring the particulate matter collected by the filter in each of the running steps.

Such an exhaust gas measurement method can produce the same working effect as that of the above-described exhaust gas measurement system.

Advantageous Effects of Invention

According to the present invention configured as described, in addition to making it possible to accurately measure the mass of the PM, the dilution ratio accuracy of the diluted exhaust gas can be secured.

DETAILED DESCRIPTION

One embodiment of the exhaust gas measurement system according to the present invention will be described below.

An exhaust gas measurement system 100 of the present embodiment is one adapted to measure particulate matter (hereinafter also referred to as PM) contained in the exhaust gas of an unillustrated internal combustion engine, and here configured to collect and dilute part of the exhaust gas discharged from the internal combustion engine, and then conduct the total amount of the collected and diluted exhaust gas to a filter F.

Note that the exhaust gas measurement system 100 can be mounted in a vehicle in running on a road, and this makes it possible to measure the PM contained in the exhaust gas discharged from the internal combustion engine during actual on-road running.

Figure 1:
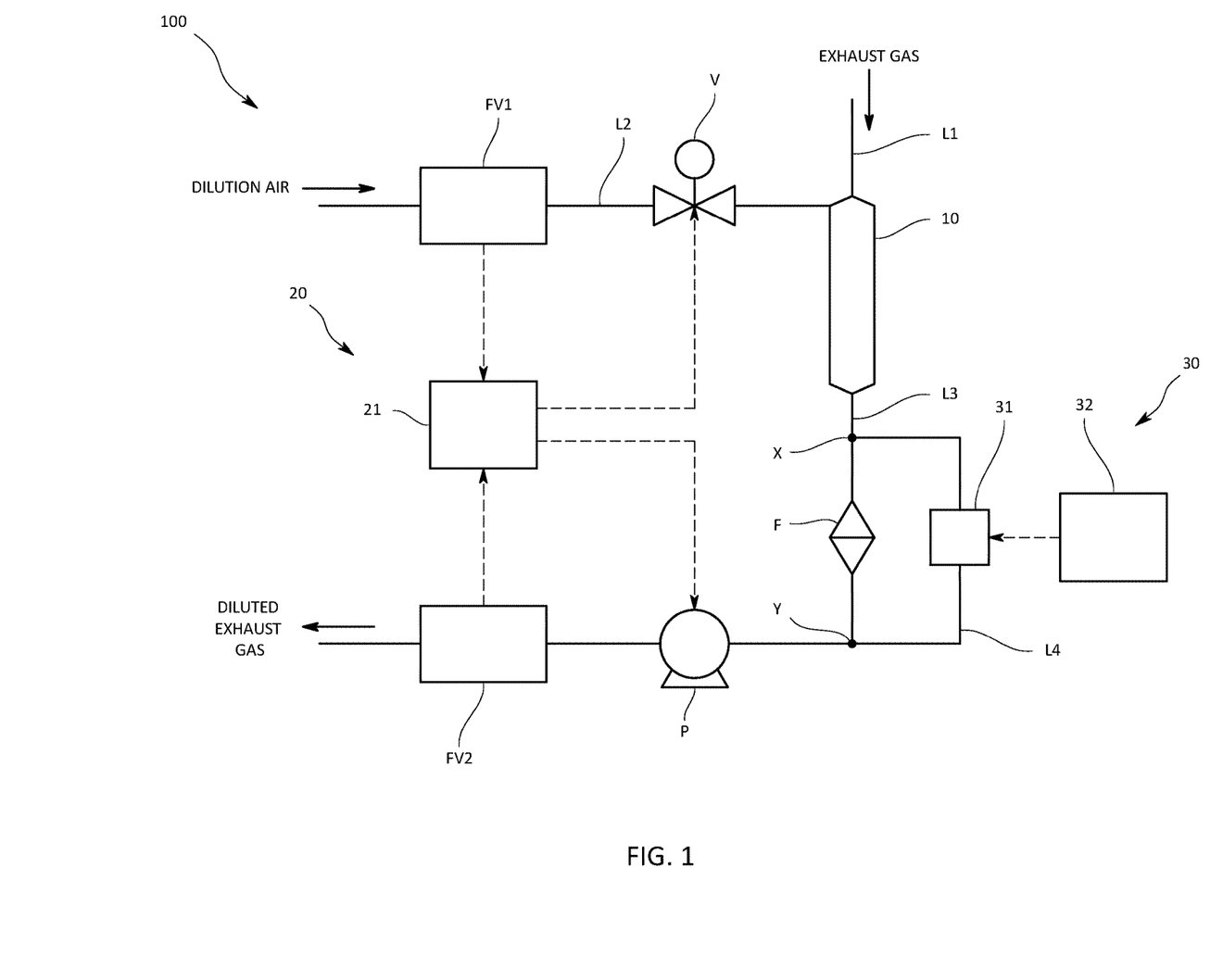
FIG. 1 is a diagram schematically illustrating the configuration of an exhaust gas measurement system of the present embodiment.

Specifically, as illustrated in FIG. 1, the exhaust gas measurement system 100 is one including: an exhaust gas introduction path L1 into which the exhaust gas of the internal combustion engine is introduced; a diluent gas flow path L2 through which diluent gas for diluting the exhaust gas flows; a dilution tunnel 10 that is connected with the exhaust gas introduction path L1 and the diluent gas flow path L2; a diluted exhaust gas flow path L3 through which diluted exhaust gas produced in the dilution tunnel 10 flows; and a flow rate control mechanism 20 adapted to control the flow rates of the diluent gas and diluted exhaust gas.

The exhaust gas introduction path L1 is one that is connected into, for example, an unillustrated exhaust pipe of the internal combustion engine to collect the part of the exhaust gas discharged from the internal combustion engine in a flow separation manner and conducts the collected exhaust gas to the dilution tunnel 10.

The diluent gas flow path L2 is one adapted to conduct the diluent gas to the dilution tunnel 10, of which one end is connected to an unillustrated diluent gas source and the other end is connected to the dilution tunnel 10.

In addition, in the present embodiment, the diluent gas is air.

The dilution tunnel 10 is one adapted to produce the diluted exhaust gas by diluting the exhaust gas at a predetermined dilution ratio, and here a so-called micro tunnel.

Note that the dilution tunnel 10 may be a so-called full tunnel to which the total amount of the exhaust gas discharged from the internal combustion engine is conducted.

The diluted exhaust gas flow path L3 is one of which the starting end is connected to the dilution tunnel 10 and through which the diluted exhaust gas flows, and configured to collect PM contained in the diluted exhaust gas by, for example, the one filter F provided in the diluted exhaust gas flow path L3.

Note that the other end of the diluted exhaust gas flow path L3 may be opened to the air or connected to various exhaust gas analyzers.

The flow rate control mechanism 20 is one adapted to control the flow rates of the diluent gas and diluted exhaust gas as described above, and includes: a diluent gas flowmeter FV1 and flow rate control valve V that are provided in the diluent gas flow path L2; a diluted exhaust gas flowmeter FV2 and a suction pump P (e.g., a roots blower) of which suction capability can be varied by controlling a rotation speed, both of which are provided on the downstream side of the filter F in the diluted exhaust gas flow path L3; and a control device 21 adapted to control the flow rate control valve V and the suction pump P.

In addition, the diluent gas flowmeter FV1 and the diluted exhaust gas flowmeter FV2 in the present embodiment are both venturi flowmeters.

The control device 21 is one that physically includes some components such as a CPU, a memory, an A/D converter, and a D/A converter, and obtains flow rate signals indicating measurement values of the respective flowmeters FV1 and FV2 as well as functioning to control the flow rate control valve V and the suction pump P on the basis of the flow rate signals by making the CPU and peripheral devices cooperate in accordance with a program stored in a predetermined area of the memory.

Specifically, the control device 21 calculates the difference between the diluted exhaust gas flow rate and the diluent gas flow rate as an exhaust gas sampling flow rate and also feedback controls the dilution ratio calculated from the sampling flow rate and the diluent gas flow rate.

Further, as illustrated in FIG. 1, the exhaust gas measurement system 100 of the present embodiment is adapted to further include: a bypass flow path L4 that branches from the upstream side of the filter F in the diluted exhaust gas flow path L3 and merges with the downstream side of the filter F; and a separation flow rate control part 30 that while flowing the diluted exhaust gas through the filter F, controls a separation flow rate through the bypass flow path L4.

The bypass flow path L4 is one that bypasses the filter F without flowing part of the diluted exhaust gas through the filter F, and branches from a branching point X between the dilution tunnel 10 and the filter F and merges at a merging point Y between the filter F and the suction pump P. Incidentally, if the merging point Y of the bypass flow path L4 is provided on the downstream side of the suction pump P, in order to conduct the part of the diluted exhaust gas to the bypass flow path, it is necessary to separately provide a suction pump in the bypass flow path L4 or on the downstream side of the merging point Y. On the other hand, in the present embodiment, as described above, since the merging point Y is provided between the filter F and the suction pump P, i.e., on the upstream side of the suction pump P, the difference in pressure between the branching point X and the merging point Y can conduct the part of the diluted exhaust gas to the bypass flow path L4 without separately providing a suction pump in the bypass flow path L4 or another position.

The separation flow rate control part 30 is one that controls the separation flow rate through the bypass flow path L4 in order to change the flow rate of the diluted exhaust gas flowing through the filter F, and has a mass flow controller 31 provided in the bypass flow path L4 and a control part main body 32 adapted to control the mass flow controller 31.

In addition, the mass flow controller 31 in the present embodiment is of a differential pressure type, but a thermal type one may be used.

Figure 2:
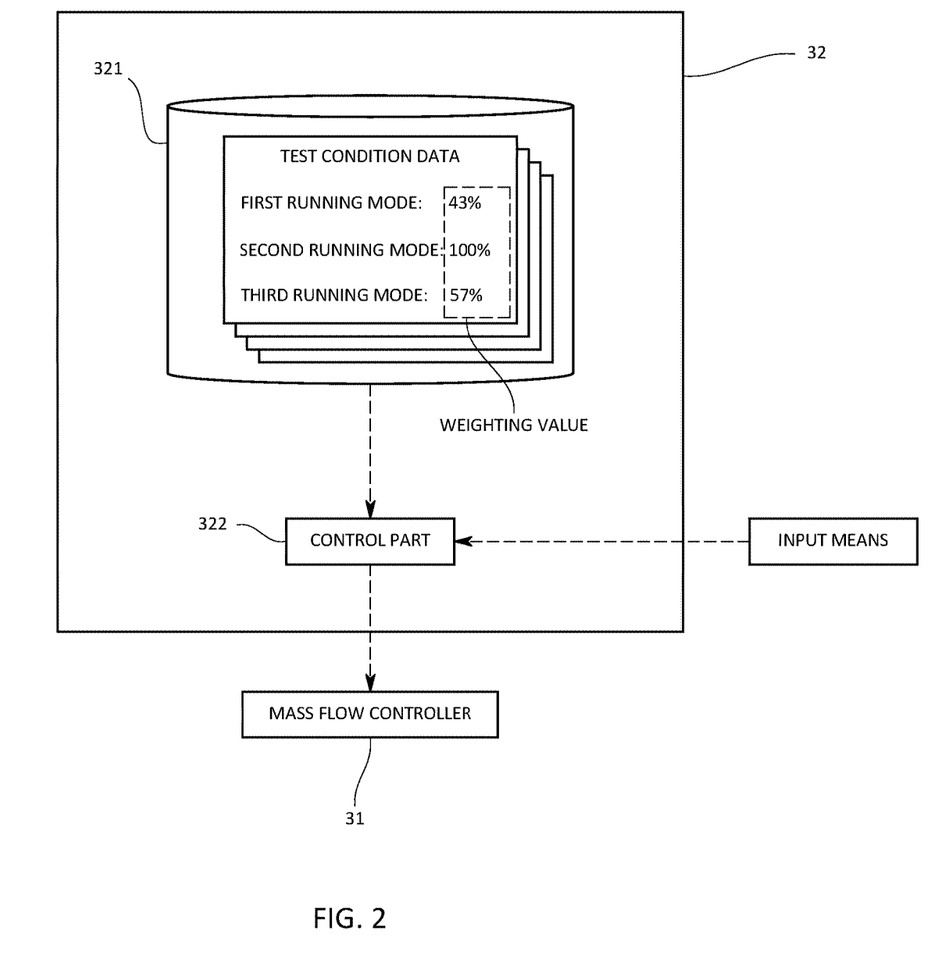
FIG. 2 is a functional block diagram illustrating functions of a control part main body in the same embodiment.

The control part main body 32 is one that physically includes some components such as a CPU, a memory, an A/D converter, and a D/A converter, and as illustrated in FIG. 2, configured to function as a test condition storage part 321 and a control part 322 by making the CPU and peripheral devices cooperate in accordance with a program stored in a predetermined area of the memory.

In the following, while referring to FIG. 2 and a flowchart in FIG. 3, the detailed description of the respective parts will be given in combination with the description of the actions of the control main body 32.

As illustrated in FIG. 2, the test condition storage part 321 is set in a predetermined area of the memory, and stores pieces of test condition data each indicating test conditions that are preliminarily set in order to obtain a test result. Note that the test conditions refer to ones such as test conditions stipulated in regulations, emissions measurement regulations, or the like, or test conditions arbitrarily set by an operator, and the test condition storage part 321 in the present embodiment stores the multiple pieces of test condition data.

As each piece of test condition data, the test condition storage part 321 in the present embodiment stores: multiple running modes each indicating a vehicle running state; and flow rate conditions on the flow rate of the diluted exhaust gas to be flowed through the filter F in the respective running modes with the running modes linked with the flow rate conditions, respectively.

The flow rate conditions refer to weighting values determined for the mass of PM measured in corresponding ones of the running modes in order to obtain one test result, and here weighting values stipulated in regulations such as CFR 1066.

That is, the test condition storage part 321 stores the multiple running modes and the weighting values predetermined corresponding to the respective running mode with the running modes linked with the weighting values, respectively and correspondingly.

More specifically, the three running modes and the weighting values corresponding to the respective running modes are stored as one piece of test condition data with the running modes linked with the weighting values, respectively, and for example, the weighting values in the first, second, and third running modes are set to 43%, 100%, and 57%, respectively.

Figure 3:
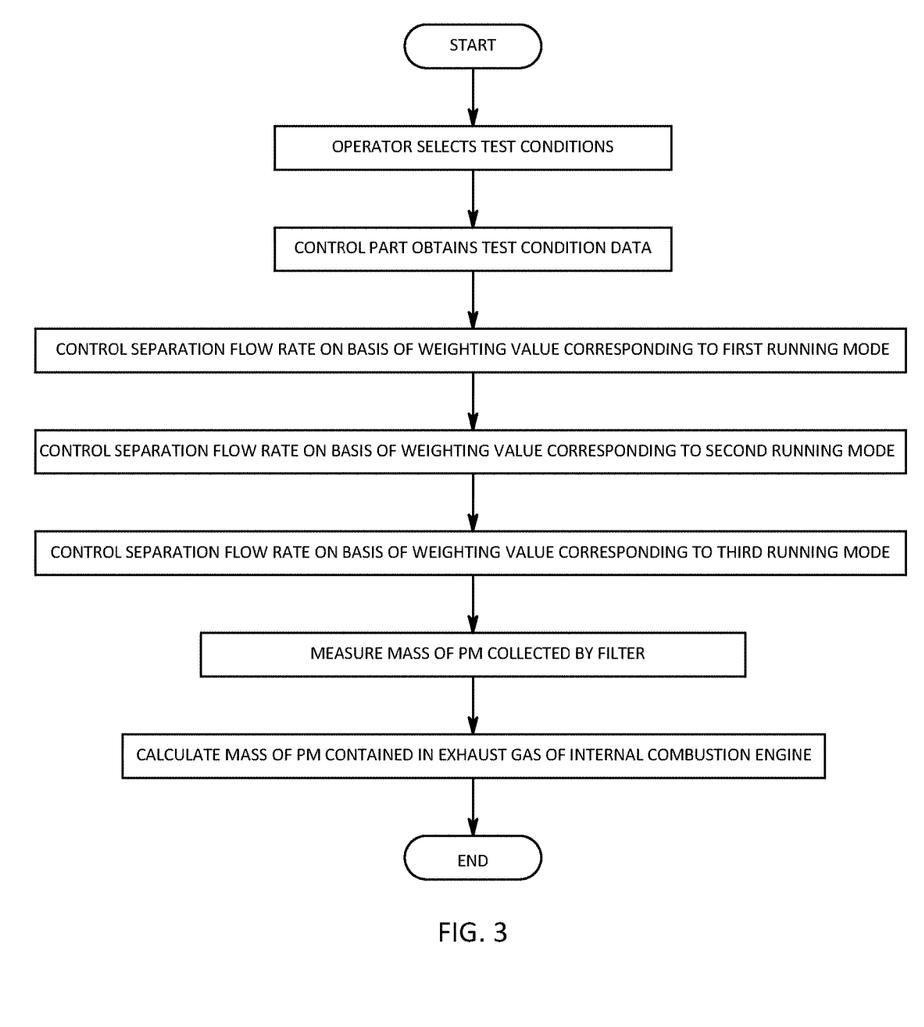
FIG. 3 is a flowchart for explaining the actions of the exhaust gas measurement system of the same embodiment.

The control part 322 is one that as illustrated in FIG. 3, from the test condition storage part 321, obtains test condition data indicating test conditions selected by, for example, an operator using input means, as well as controlling the separation flow rate on the basis of the test condition data.

In more detail, in each running mode, the control part 322 is adapted to transmit a control signal to an unillustrated flow rate control valve of the mass flow controller 31 provided in the bypass flow path L4, and make the flow rate of the diluted exhaust gas flowing through the filter F equal to a flow rate calculated by multiplying a predetermined reference flow rate by a weighting value corresponding to that running mode.

More specifically, the control part 322 is adapted to make the ratio in the flow rate of the diluted exhaust gas flowing through the filter F, i.e., the ratio among a first flow rate in the first running mode, a second flow rate in the second running mode, and a third flow rate in the third running mode equal to the above-described weighting value ratio, i.e., 43:100:57.

The present embodiment is adapted to continuously switch among the first, second, and third modes, and allow the diluted exhaust gas flowing under a flow rate condition corresponding to each of the running modes to pass through the one common filter F.

As described, after the diluted exhaust gas has flowed through the filter F in each of the running modes, an operator removes the above-described filter F to measure the mass of collected PM, and on the basis of the resulting measurement value and the dilution ratio of the diluted exhaust gas, can calculate the mass of the PM contained in the exhaust gas.

The exhaust gas measurement system 100 according to the present embodiment configured as described can weight the flow rate of the diluted exhaust gas flowing through the filter F by controlling the separation flow rate, and can therefore accurately measure the mass of the PM using the filter F common to the respective running modes.

In addition, since only the flow rate of the diluted exhaust gas flowing through the filter F can be weighted without changing the total flow rate of the diluted exhaust gas, the flow rates of the diluent gas and diluted exhaust gas can be accurately measured using the venturi flowmeters as the diluent gas flowmeter FV1 and the diluted exhaust gas flowmeter FV2, and therefore the dilution ratio accuracy of the diluted exhaust gas can be secured.

Also, since the flow rate of the diluted exhaust gas flowing through the filter F can be weighted without changing the flow rate of the diluted exhaust gas on the upstream side of the branching point X, the retention time of the diluted exhaust gas on the upstream side of the filter F can be made constant independently of any test condition, and the retention time can be prevented from falling outside test conditions.

Further, since the venturi flowmeters are used as the diluent gas flowmeter FV1 and the diluted exhaust gas flowmeter FV2, respectively, the flow rates of the diluent gas and diluted exhaust gas can be accurately measured, and therefore the dilution ratio can be more accurately controlled.

Incidentally, even if each of the venturi flowmeter has only a range of approximately 50%, as described above, the flow rate of the diluted exhaust gas flowing through the filter F can be weighted without changing the flow rates through the respective venturi flowmeters, and therefore the dilution ratio accuracy can be secured independently of a weighting value.

In addition, since the exhaust gas measurement system 100 of the present embodiment can be mounted in a vehicle in running on a road, a test complying with regulations can be done in one run during actual on-road running without replacing the filter F.

Note that the present invention is not limited to the above-described embodiment.

For example, in the above-described embodiment, a flow rate condition corresponding to each of the running modes is a weighting value stipulated in regulations, but may be, for example, a flow rate or flow rate ratio arbitrarily determined by an operator.

Figure 4:
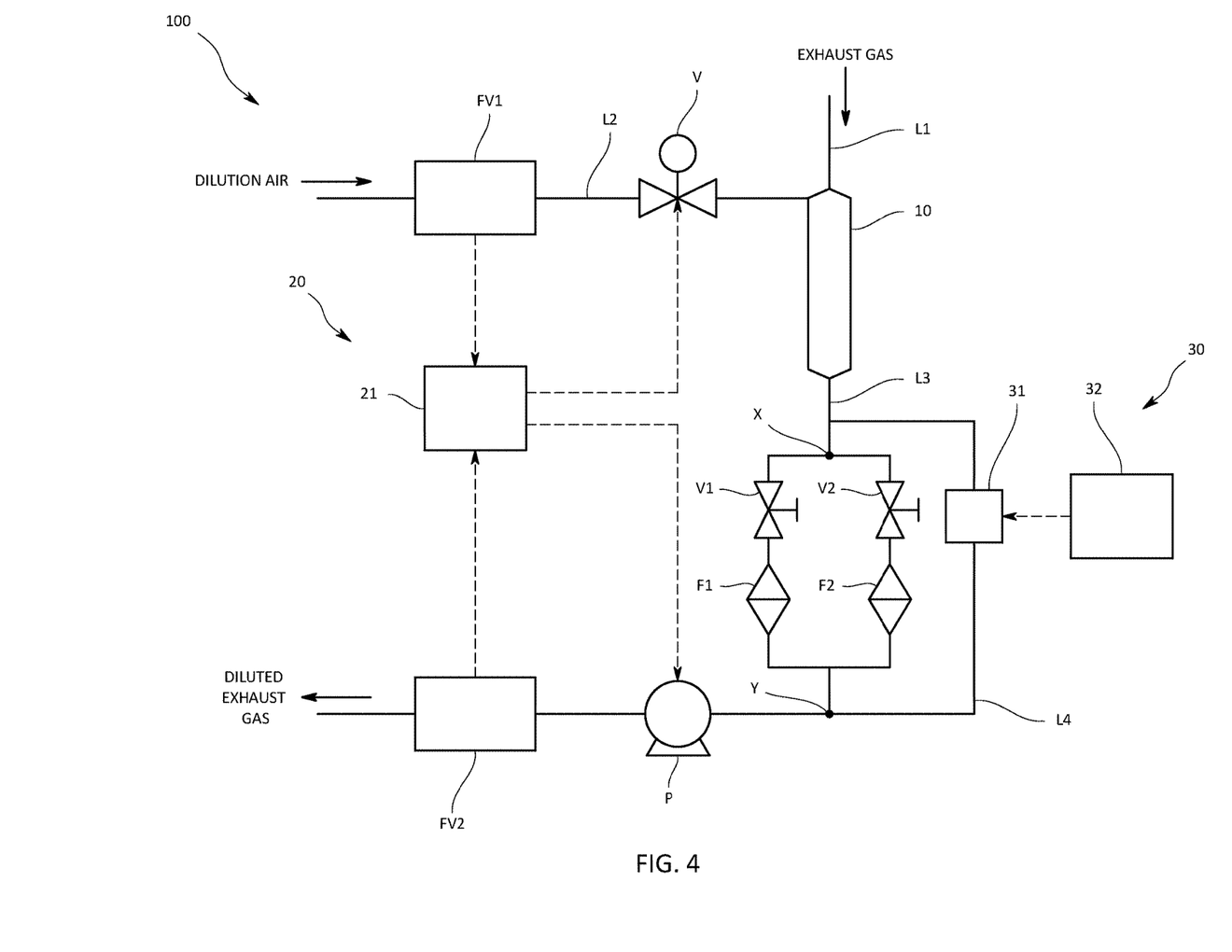
FIG. 4 is a diagram schematically illustrating the configuration of an exhaust gas measurement system of a variation.

Also, in the above-described embodiment, the one filter is provided in the diluted exhaust gas flow path; however, as illustrated in FIG. 4, multiple filters F1 and F2 may be provided in parallel in the diluted exhaust gas flow path L3.

In this configuration, by switching between on/off valves V1 and V2 provided corresponding to the respective filters F1 and F2, for example, when replacing one of the filters F1 and F2, the diluted exhaust gas can be kept flowing through the other filter F2 or F1.

Note that the diluted exhaust gas flow path is not necessarily required to be provided with a filter, but may be adapted to be provided with, for example, a continuous PM meter, or any other various exhaust gas analyzers to measure the PM in the diluted exhaust gas.

Further, the flow rate control mechanism may be one having mass flow controllers respectively provided in the diluent gas flow path and the diluted exhaust gas flow path.

Note that the measurement accuracy of a mass flow controller is easily affected by exhaust gas, and therefore in order to accurately control the flow rates of the diluent gas and diluted exhaust gas, it is preferable to have venturi flowmeters as with the flow rate mechanism in the above-described embodiment.

The test condition storage part in the above-described embodiment is one that stores the multiple pieces of test condition data, but may be one that stores only one piece of test condition data.

In addition, in the above-described embodiment, the control device and the control part main body are separated, but may be physically integrated to make the control device have the functions of the control part main body, or to make the control part main body have the functions of the control device.

Further, the exhaust gas measurement system of the above-described embodiment is one having the one dilution tunnel, but may be one configured to have multiple dilution tunnels and dilute the exhaust gas discharged from the internal combustion engine in a multistep manner.

Still further, the separation flow rate control part is not necessarily required to have the control part main body, but may be configured to have, for example, only the flow rate control valve provided in the bypass flow path.

In this configuration, it is only necessary that in each of the running modes, in order to weight the flow rate of the diluted exhaust gas flowing through the filter, for example, a flow rate sensor or the like is provided in the bypass flow path, and an operator adjusts a valve opening level of the flow rate control valve while checking the value of the flow rate sensor or the like.

When doing this, in order to adjust the valve opening level in a state where a vehicle is stopped running, it is only necessary to, for example, while flowing only the diluent gas, compare the flow rate of the diluent gas flowing through the filter and the separation flow rate through the bypass flow path with each other.

Also, in order to perform the flow rate control by the mass flow controller 31, the control part main body may be configured to, in response to a change of a gas species, obtain a conversion factor (gas species correction factor) for calculating a flow rate value corresponding to a changed gas species, and correct the mass flow controller 31 using the conversion factor.

Figure 5:
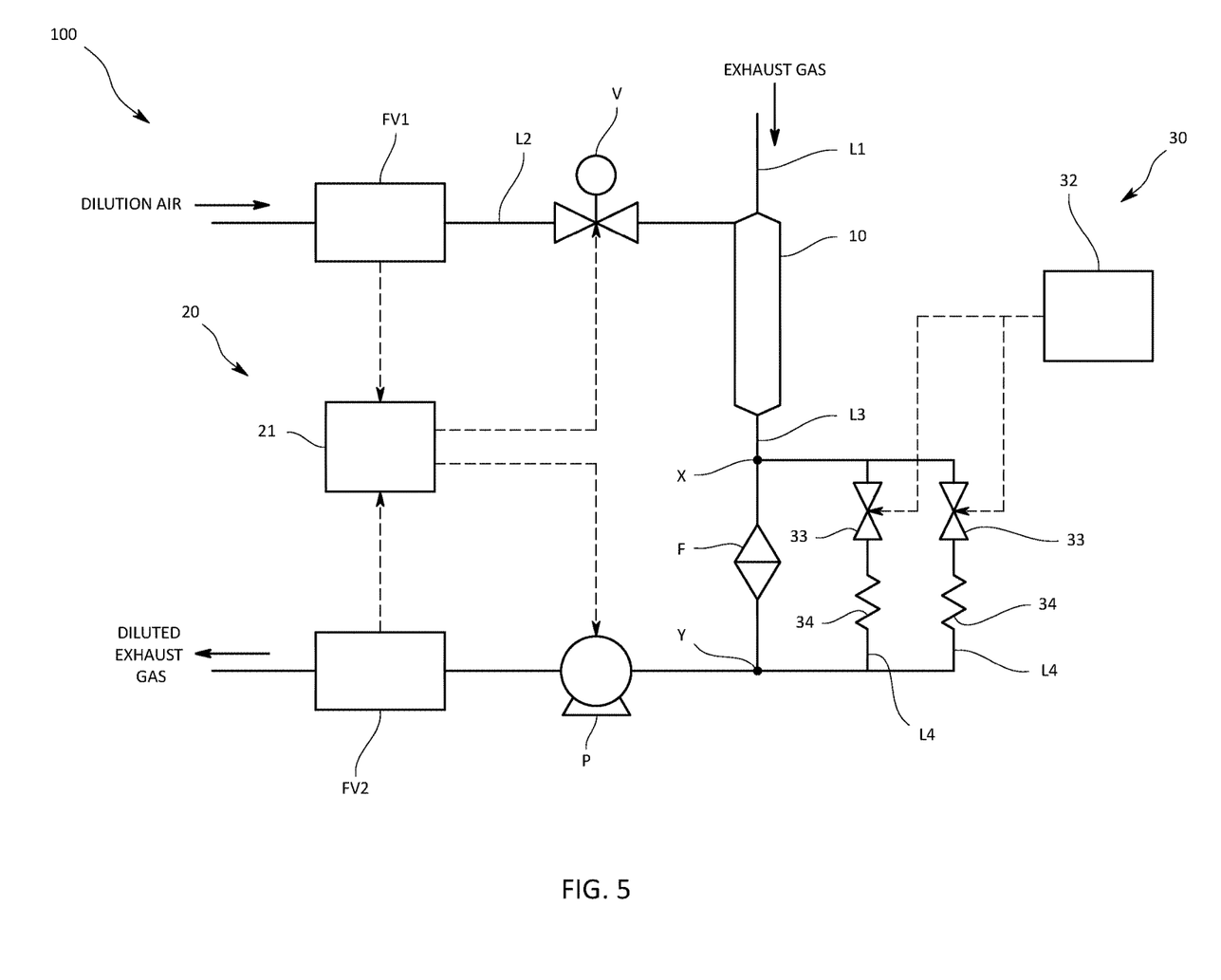
FIG. 5 is a diagram schematically illustrating the configuration of an exhaust gas measurement system of another variation.

In addition, the separation flow rate control part 30 may be one that as illustrated in FIG. 5, has: multiple bypass flow paths L4 adapted to allow the part of the diluted exhaust gas to bypass the filter F; an on/off valve 33 (e.g., a solenoid valve) and a constant flow rate device 34 (such as an orifice) that are provided in each of the bypass flow paths L4; and a control part main body 32 adapted to output an on/off signal to each of the on/off valves 33.

In the above-described configuration, for example, by using orifices having mutually different opening sizes as the constant flow rate devices 34 to control on/off of the on/off valves 33, respectively, a flow rate through the filter F and flow rates through the respective bypass flow paths L4 can be controlled to have a predetermined flow rate ratio, and the flow rate of the diluted exhaust gas flowing through the filter F can be weighted.

Besides, it should be appreciated that the present invention is not limited to any of the above-described embodiment and variations, but can be variously modified without departing the scope thereof.

REFERENCE SIGNS LIST

100: Exhaust gas measurement system
F: Filter
10: Dilution tunnel
L3: Diluted exhaust gas flow path
L4: Bypass flow path
30: Separation flow rate control part
31: Mass flow controller
32: Control part main body

What is claimed is:

1. An exhaust gas measurement system comprising:
    a diluted exhaust gas flow path through which diluted exhaust gas flows, wherein the diluted exhaust gas is produced by diluting exhaust gas with diluent gas;
    a valve through which the diluent gas flows in fluid communication with the diluted exhaust gas flow path;
    a processor that obtains flow rate signals indicating flow rates of the diluted exhaust gas and diluent gas, and feedback controls the valve on a basis of the flow rate signals to control a dilution ratio associated with the diluted exhaust gas and diluent gas;
    a common filter in the diluted exhaust gas flow path that collects particulate matter from the diluted exhaust gas flowing through the common filter for measurement;
    a bypass flow path that branches from an upstream side of the common filter in the diluted exhaust gas flow path and merges with a downstream side of the common filter;
    a memory that stores test condition data including multiple running modes each indicating a vehicle running state and weighting values predetermined for the respective multiple running modes; and
    a separation flow rate control part that obtains the test condition data from the memory, and that adjusts a separation flow rate of the diluted exhaust gas flowing through the bypass flow path based on the weighting values included in the test condition data to change the flow rate of the diluted exhaust gas flowing through the common filter, wherein the diluted exhaust gas flows through the common filter before and after the change.

2. The exhaust gas measurement system according to claim 1, wherein:
    a flow rate condition on the flow rate of the diluted exhaust gas flowing through the common filter is determined in accordance with the test condition data; and
    the separation flow rate control part on a basis of the flow rate condition, adjusts the separation flow rate.

3. The exhaust gas measurement system according to claim 2, wherein:
    the flow rate condition is determined on a basis of the weighting values.

4. The exhaust gas measurement system according to claim 3, wherein in all the multiple running modes, the diluted exhaust gas flows through the common filter.

5. The exhaust gas measurement system according to claim 3, wherein the predetermined weighting values corresponding to a first, second, and third of the multiple running modes are set such that a ratio among a first flow rate of the diluted exhaust gas flowing through the common filter in the first of the multiple running modes, a second flow rate of the diluted exhaust gas flowing through the common filter in the second of the multiple running modes, and a third flow rate of the diluted exhaust gas flowing through the common filter in the third of the multiple running modes is 43:100:57.

6. An exhaust gas measurement method comprising:
flowing at a first flow rate diluted exhaust gas through a diluted exhaust gas flow path that includes a common filter that collects particulate matter from the diluted exhaust gas;
feedback controlling a valve in fluid communication with the diluted exhaust gas flow path on a basis of flow rate signals indicating flow rates of a diluent gas flowing through the valve and the diluted exhaust gas to control a dilution ratio associated with the diluted exhaust gas and diluent gas;
storing in memory test condition data including multiple running modes each indicating a vehicle running state and weighting values predetermined for the respective multiple running modes;
obtaining the test condition data from the memory;
adjusting based on the weighting values included in the test condition data a separation flow rate of the diluted exhaust gas, flowing through a bypass flow path that branches from an upstream side of the common filter in the diluted exhaust gas flow path and merges with a downstream side of the common filter, to change the flow rate of the diluted exhaust gas flowing through the common filter; and
measuring the particulate matter collected by the common filter.

* * * * *